(12) United States Patent
Kamada et al.

(10) Patent No.: US 7,364,701 B1
(45) Date of Patent: Apr. 29, 2008

(54) LIQUID HOMOGENIZING UNIT AND HIGH SPEED LIQUID CHROMATOGRAPH EQUIPPED WITH THE SAME

(75) Inventors: Takanori Kamada, Kyoto (JP); Kazunori Hirose, Kyoto (JP)

(73) Assignee: Arkray, Inc., Kyoto (JP)

( * ) Notice: Subject to any disclaimer, the term of this patent is extended or adjusted under 35 U.S.C. 154(b) by 426 days.

(21) Appl. No.: 10/089,399

(22) PCT Filed: Sep. 28, 2000

(86) PCT No.: PCT/JP00/06744

§ 371 (c)(1),
(2), (4) Date: Jul. 22, 2002

(87) PCT Pub. No.: WO01/23879

PCT Pub. Date: Apr. 5, 2001

(30) Foreign Application Priority Data

Sep. 29, 1999 (JP) .................................. 11-276450

(51) Int. Cl.
*B01F 5/00* (2006.01)

(52) U.S. Cl. ........................ 422/99; 422/70; 422/82.05; 422/82.09; 356/246; 366/143; 366/165.1; 366/341

(58) Field of Classification Search ............... 422/70, 422/82.05, 82.09, 99; 436/161, 164, 66, 436/67; 356/246; 366/143, 165.1, 341
See application file for complete search history.

(56) References Cited

U.S. PATENT DOCUMENTS 3,520,517 A    7/1970   Hrdina
3,822,947 A *  7/1974   Aday, Jr. .................... 356/246
5,474,677 A   12/1995   Naka
6,122,049 A    9/2000   Sugiyama et al.

FOREIGN PATENT DOCUMENTS

| | | |
|---|---|---|
| DE | 91 07 564 | 9/1991 |
| FR | 1 449 409 A | 8/1966 |
| GB | 2 089 062 A | 6/1982 |
| JP | 09-274029 | 10/1997 |
| JP | 11-166886 A | 6/1999 |

OTHER PUBLICATIONS

Machine translation of JP 11-166886 http://www4.apdl.ncipi.go.jp/cgi-bin/tran_web_cgi_ejje.*
http://www.answers.com/topic/integral.*
http://www.thefreedictionary.com/axis.*

* cited by examiner

*Primary Examiner*—Jan M. Ludlow
(74) *Attorney, Agent, or Firm*—Hamre, Schumann, Mueller & Larson, P.C.

(57) ABSTRACT

A liquid homogenizing unit comprising a feed flow channel (56), a discharge flow channel (57), a first intermediate flow channel (58) communicating with the feed flow channel (56), and a second intermediate flow channel (55) communicating will the first intermediate flow channel (58) and discharge flow channel (57). The first intermediate flow channel (58) extends in a direction which crosses the second intermediate flow channel (55).

4 Claims, 8 Drawing Sheets

LIQUID HOMOGENIZING UNIT AND HIGH SPEED LIQUID CHROMATOGRAPH EQUIPPED WITH THE SAME

TECHNICAL FIELD

The present invention relates to a liquid homogenizing unit which is incorporated into a liquid flow system, and which positively generates an eddy current in the liquid. The invention also relates to a high-performance liquid chromatography apparatus which is equipped with such a liquid homogenizing unit.

BACKGROUND ART

High-performance liquid chromatography (hereafter referred to as "HPLC") is known as a chemical separation method utilizing a liquid flow system. HPLC can be used for various types of chemical analysis, and various types of HPLC apparatus have been developed according to the applications involved. One such apparatus is a glycosylated hemoglobin measuring apparatus which is used to diagnose diabetes. This measuring apparatus uses blood as a sample, and generally measures the proportion of hemoglobin A1c (hereafter referred to as "HbA1c") relative to the total amount of hemoglobin contained in the blood. In concrete terms, in this apparatus, a sample solution is prepared by diluting blood with an appropriate diluent, and respective hemoglobin components such as HbA1c and the like contained in the sample solution are developed inside a column using an eluant. As a result, the respective hemoglobin components contained in the sample solution are eluted from the column as separated from each other. The absorbance of the eluate that flows out of the column is constantly measured by a detector which is installed downstream from the column. The absolute values of the HbA1c and other hemoglobins that are eluted from the column are determined on the basis of the absorbance thus measured. Furthermore, the apparatus finally calculates the proportion of HbA1c relative to the total amount of hemoglobin including the HbA1c.

However, in the glycosylated hemoglobin measuring device consisting of a conventional HPLC apparatus, the measured value of the HbA1c fluctuates according to the dilution rate of the blood. In the case of HbA1c originating from the same blood, it would be expected that the measurement results in the same proportion for the HbA1c regardless of the dilution rate of the blood, i.e., regardless of the blood concentration in the sample. In reality, however, the measured value differs according to the blood concentration, so that a fixed value cannot be obtained.

The cause of this problem is thought to be as follows. In cases where the concentrations of the hemoglobin components contained in the eluate varies with the passage of time, the concentration distribution in becomes non-uniform in the radial cross section of the flow path of the eluate that flows through the measurement flow path of the detector. In the piping that extends from the outlet of the column to the measurement flow path of the detector, the eluate is subjected to resistance from the wall surfaces of the piping. As a result, the flow velocity of the eluate becomes slower in the peripheral portions of the cross section of the piping than in the central portion. This state is also maintained inside the measurement flow path. Accordingly, in cases where the hemoglobin concentration in the eluate increases with the passage of time, the progress of liquid substitution is slower in the vicinity of the wall surfaces of the measurement flow path than in the cross-sectionally central portion of the flow path, so that a lower hemoglobin concentration tends to be maintained. As a result, the eluate that flows through the measurement flow path has a concentration gradient that drops from the cross-sectionally central portion of the flow path toward the cross-sectionally peripheral portions. When the absorbance of the eluate inside the measurement flow path is measured in a state in which such a concentration gradient is formed inside the measurement flow path, a value that is lower than the value that should be measured in an ideal state of the eluate in which no concentration gradient is formed is actually measured.

The deleterious effects arising from such laminar flow are especially severe in cases where an extreme variation is seen in the concentration of the eluate over time. Accordingly, in the measurement of glycosylated hemoglobin, the measurement of hemoglobin A0 (hereafter referred to as "HbA0"), which assumes the major portion of the hemoglobin in the blood, and which is the hemoglobin component that is eluted most slowly from the column, is most affected. The effect on HbA0, which has a high concentration in the blood, is much greater than the effect on other hemoglobins such as HbA1c and the like, which have a low concentration. The apparent reason for this is that if the amount of HbA0 present in the largest amounts is measured as a value that is smaller than the true value, then the overall amount of hemoglobin that is present will be estimated on the low side. As a result, the ratio of HbA1c that is present will be calculated on the high side. This view agrees with the experimental rule that the measured value of HbA1c increases with an increase in the concentration of the sample.

If a sufficiently long time is taken for separation by means of a column, the rate of variation in the HbA0 concentration is reduced. Accordingly, the effects of the laminar flow can be alleviated. In this case, however, the separation peaks originating from the respective hemoglobin components tend to overlap in the chromatogram, which is undesirable. Furthermore, such a process is also undesirable in that more time and a greater amount of eluant are required. Especially in the case of a glycosylated hemoglobin measuring apparatus utilizing HPLC, a shortening of the measurement time is desirable. Accordingly, the expenditure of a considerable amount of time on separation by means of a column conflicts with this requirement, and is undesirable.

In the past, a glycosylated hemoglobin measuring apparatus equipped with a diffusion coil has been proposed in order to alleviate the above-mentioned problems occurring inside the measurement flow path of the detector. This diffusion coil is a helical pipe, and is disposed in a position located near the detector in which the measurement flow path is formed. This diffusion coil generates a convection current inside the eluate from the column. As a result, the hemoglobin contained in the eluate is positively diffused in three dimensions. As a result of the diffusing action caused by such a convection current inside the diffusion coil, the concentration gradient in the flow path cross section of the eluate flowing through the measurement flow path is alleviated, so that the measured value of the HbA0 is stabilized to a constant value.

However, although the measured value of the high-concentration component HbA0 can be stabilized to a constant value in the case of a conventional glycosylated hemoglobin measuring apparatus using a diffusion coil, such an apparatus suffers from the following problems. First, since a dilute solution which is by nature relatively immune to the effects of laminar flow is also affected by the convection effect of the diffusion coil, peaks originating from low-concentration hemoglobin components are blunted. Such low-concentration hemoglobin components include HbA1c. As a result, the analytical performance of the apparatus as a glycosylated hemoglobin measuring apparatus drops. Secondly, if a diffusion coil is used, the eluate is subjected to a convection effect before the eluate flows into the measurement flow path. Accordingly, in the eluate that has flowed into the measurement flow path, the hemoglobin components are diffused to a considerable extent not only in the radial direction, but also in the flow direction. As a result of this diffusion in the flow direction, the degree of separation of components that have already once been separated by the column is reduced in the piping that follows the column. As a result, the half-value widths of the peaks originating from the respective components are broadened in the chromatogram, so that the analysis time is increased beyond the conventional value relative to the time required for separation.

DISCLOSURE OF THE INVENTION

It is an object of the present invention to eliminate or alleviate the above-mentioned problems.

In a first aspect of the present invention, a liquid homogenizing unit is provided. The liquid homogenizing unit comprises a supply flow path and a discharge flow path, a first intermediate flow path which communicates with the supply flow path, and a second intermediate flow path which communicates with the first intermediate flow path and the discharge flow path. The first intermediate flow path extends in an intersecting direction relative to the second intermediate flow path.

Preferably, the second intermediate flow path is substantially cylindrical, and the first intermediate flow path is connected to the second intermediate flow path in a position that is offset from the axis of the second intermediate flow path.

Preferably, the first intermediate flow path tapers from the supply flow path toward the second intermediate flow path.

Preferably, the first intermediate flow path has a uniform cross section.

Preferably, the first intermediate flow path extends at right angles to the second intermediate flow path.

Preferably, the second intermediate flow path is substantially cylindrical, and the first intermediate flow path includes a first portion connected to the supply flow path and a second portion connected to the second intermediate flow path. The first portion tapers from the supply flow path toward the second portion. The second portion has a uniform cross section and is connected to the second intermediate flow path at a position that is offset from the axis of the second intermediate flow path.

Preferably, the second portion of the first intermediate flow path extends at right angles to the second intermediate flow path.

Preferably, each of the supply flow path and the second intermediate flow path has a substantially circular cross section. The first intermediate flow path includes a first portion connected to the supply flow path and a second portion connected to the second intermediate flow path. The first portion extends at an offset position from the axis of the supply flow path. The second portion flares from the first portion toward the second intermediate flow path.

Preferably, the first intermediate flow path has a smaller cross section than the second intermediate flow path.

Preferably, the supply flow path and the first intermediate flow path are connected so that these flow paths form an obtuse angle.

Preferably, the liquid homogenizing unit further comprises a unit main body which has a first end surface and a second end surface opposite to the first end surface, a first cover body, and a second cover body. The second intermediate flow path extends rectilinearly through the unit main body from the first end surface to the second end surface. The supply flow path is open toward the first end surface. The first intermediate flow path connects the supply flow path and the second intermediate flow path at the first end surface. The discharge flow path is open toward the second end surface and communicates with the second intermediate flow path. The first cover body is disposed on the first end surface to close off the supply flow path, the first intermediate flow path and the second intermediate flow path. The second cover body is disposed on the second end surface to close off the second intermediate flow path and the discharge flow path.

Preferably, each of the first and second cover bodies has a transparent part that corresponds to at least the second intermediate flow path, and the second intermediate flow path is a measurement flow path that can be used for absorbance measurement.

According to the construction of the first aspect of the present invention, when a liquid is passed through this liquid homogenizing unit, an eddy current is generated inside the second intermediate flow path. Specifically, when the liquid flows into the second intermediate flow path from the first intermediate flow path, the liquid flows through the second intermediate flow path while spiraling in an eddy. Accordingly, a solute contained in the liquid is positively diffused by the eddy current in the cross section of the second intermediate flow path.

According to a second aspect of the present invention, a high-performance liquid chromatography apparatus is provided. The high-performance liquid chromatography apparatus comprises a column and a detector for detecting the absorbance of the eluate from the column. The detector comprises a supply flow path into which the eluate from the column flows, a measurement flow path for measuring the absorbance of the eluate, a discharge flow path for discharging the eluate following the measurement of the absorbance, and an eddy current generating path for conducting the eluate having flowed into the supply flow path into the measurement flow path. The eddy current generating path extends in an intersecting direction relative to the measurement flow path, and generates an eddy current inside the measurement flow path.

Preferably, the column is supplied with a sample and an eluant as a mobile phase. The sample is prepared by diluting a analyte containing at least two components with a diluent. The ratio of at least one component contained in the analyte is measured on the basis of the absorbance detection.

Preferably, the analyte is blood. The apparatus measures the ratio of glycosylated hemoglobin contained in the hemoglobin that is present in the blood.

Preferably, the measurement flow path is substantially cylindrical, and the eddy current generating path is connected to the measurement flow path at a position that is offset from the axis of the measurement flow path.

Preferably, the eddy current generating path tapers from the supply flow path toward the measurement flow path.

Preferably, the eddy current generating path has a uniform cross section.

Preferably, the eddy current generating path extends at right angles to the measurement flow path.

Preferably, the eddy current generating path has a smaller cross section than the supply flow path or the measurement flow path.

According to the construction of the second aspect of the present invention, the same effect as that described in connection with the first aspect of the present invention can be obtained in regard to a liquid that flows through the measurement flow path of the detector. Accordingly, good absorbance measurements can be performed for a liquid that has no concentration gradient in the radial direction of the cross section of the measurement flow path.

Other features and advantages of the present invention will become clear from the detailed description that follows.

BEST MODE FOR CARRYING OUT THE INVENTION

Figure 1:
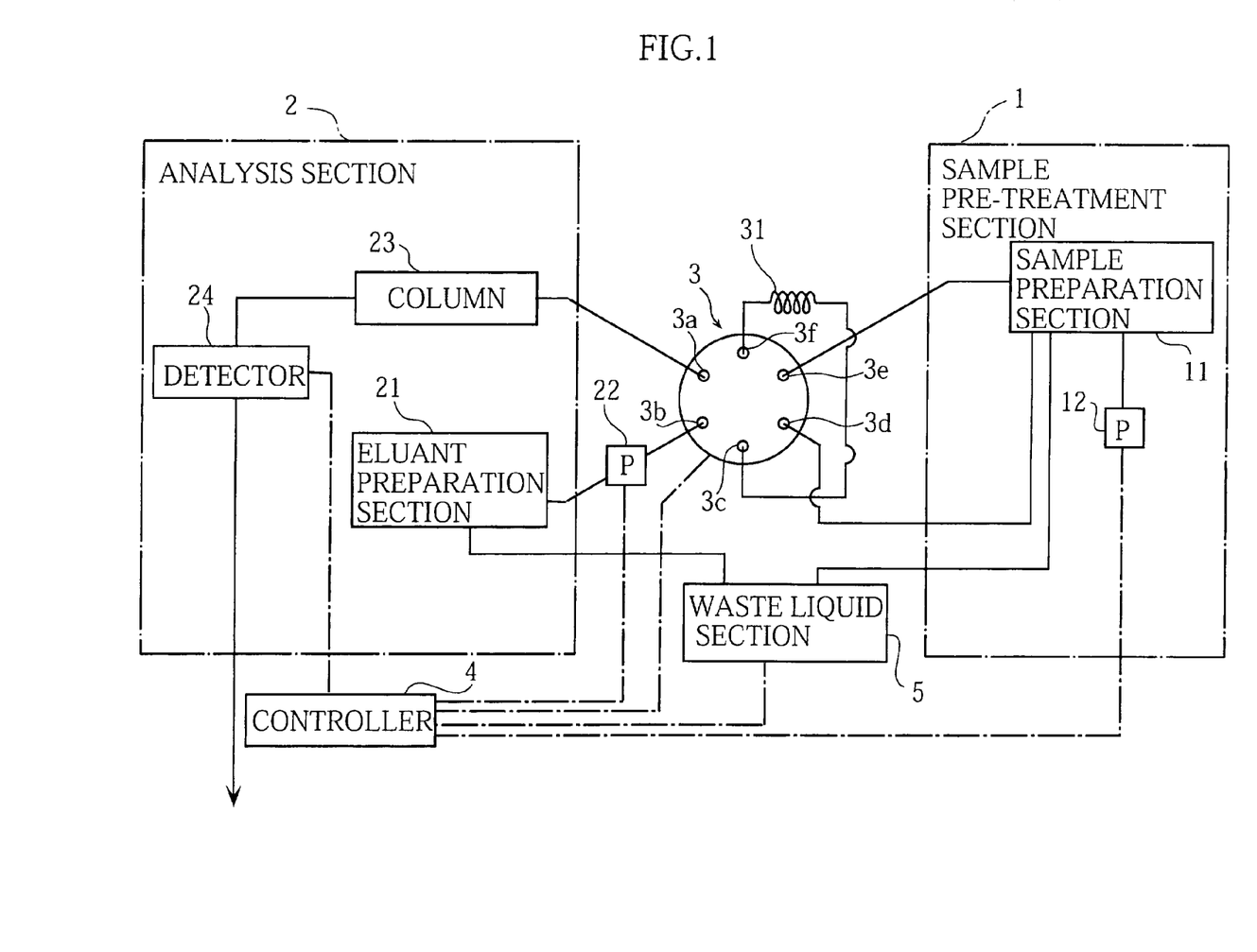
FIG. 1 is a block diagram which illustrates a glycosylated hemoglobin measuring apparatus as one example of the high-performance liquid chromatography apparatus of the present invention.

FIG. 1 is a block diagram which illustrates a glycosylated hemoglobin measuring apparatus as one example of the high-performance liquid chromatography apparatus of the present invention. This glycosylated hemoglobin measuring apparatus comprises a sample pre-treatment section 1, an analysis section 2, an injection valve 3, a controller 4 and a waste liquid section 5. The sample pre-treatment section 1 comprises a sample preparation section 11 and a liquid feeding pump 12. The analysis section 2 comprises an eluant preparation section 21, a liquid feeding pump 22, a column 23 and a detector 24. The injection valve 3 comprises an injection loop 31, and has six ports 3a-3f. The port 3a is connected to the column 23, and the port 3b is connected to the liquid feeding pump 22. The port 3c is connected to one end of the injection loop 31, and the other end of the injection loop 31 is connected to the port 3f. The ports 3d and 3e are both connected to the sample preparation section 11.

In the sample pre-treatment section 1, specified treatments are performed on the blood sample prior to analysis. During the operation of the apparatus, the prepared sample is temporarily introduced into the injection loop 31 of the injection valve 3. In the analysis section 2, the sample injected from the injection loop 31 is separated into components by the column 23; afterward, the absorbance of the solution eluted from the column 23 is measured by the detector 24. The injection valve 3 appropriately switches between a state in which the injection loop 31 is connected to the sample preparation section 11 of the sample pre-treatment section 1, and another state in which the injection loop 31 is connected to the column 23 of the analysis section 2. The controller 4 comprises a microcomputer or the like, and controls the driving of the liquid feeding pump 12 of the sample pre-treatment section 1, the liquid feeding pump 22 of the analysis section 2, the injection loop 3, and the pump, valves and the like of the waste liquid section 5. Furthermore, the controller 4 displays the measurement results on a display (not shown) in accordance with a detection signal from the detector 24, and these results are printed in a recorder (not shown). The waste liquid section 5 treats the waste liquid discharged from the sample pre-treatment section 1 and analysis section 2 during the operation of the apparatus.

The sample preparation section 11 draws in a specified amount of blood from an analyte container (not shown), and prepares a sample by diluting the blood with a specified diluent. The sample thus prepared is stored in a dilution tank (not shown) accommodated in the sample preparation section 11. The liquid feeding pump 12 feeds the sample prepared by the sample preparation section 11 into the injection loop 31 from the dilution tank via the ports 3e and 3f. The injection loop 31 has a volume sufficient to hold a specified amount of sample.

The eluant preparation section 21 prepares an eluant as a mobile phase. The eluant preparation section 21 includes a plurality of eluant tanks for storing eluants of different concentrations, and a manifold which causes the eluant flow paths from these eluant tanks to join together. The liquid feeding pump 22 feeds the eluant prepared by the eluant preparation section 21 into the column 23 via the injection valve 3. In accordance with the state of the injection valve 3, the eluant flows toward the column 23, either via the injection loop 31 or without passing through the injection loop 31. When the eluant passes through the injection loop 31, the sample that has been temporarily held inside the injection loop 31 is supplied to the column 23 together with the eluant, and is developed through the column 23 by the eluant. Since the adsorbing power with respect to the column 23 differs for each hemoglobin component contained in the sample, the time required for the respective hemoglobin components to be eluted differs. As a result, the hemoglobin is separated by the column 23 into the desired components on the basis of this difference in hemoglobin elution time. The detector 24 is equipped with a spectrophotometer or the like, and measures the absorbance of the hemoglobin-containing eluate that is eluted from the column 23.

Figure 2:
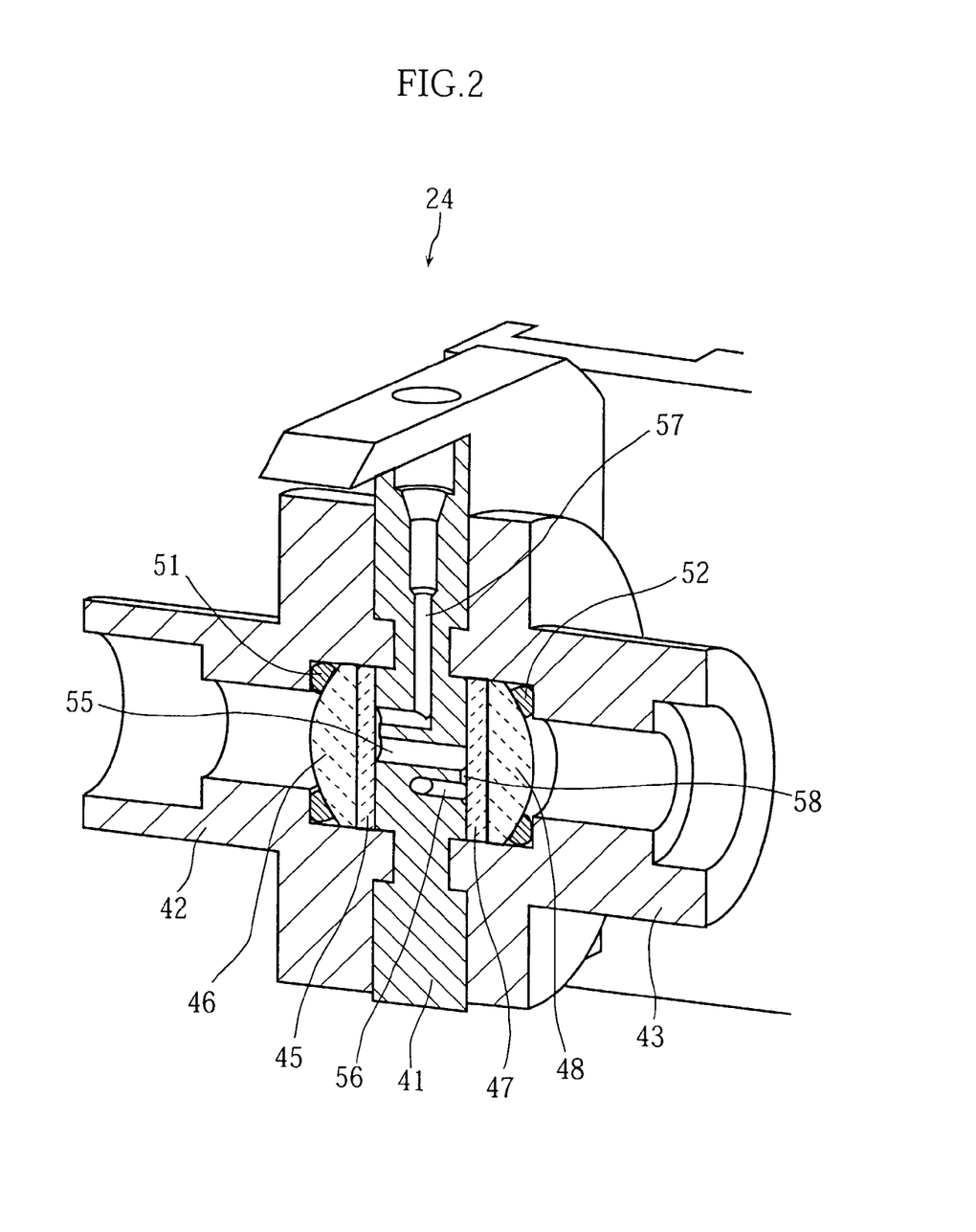
FIG. 2 is a partially sectional perspective view of the detector installed in the glycosylated hemoglobin measuring apparatus shown in FIG. 1.

FIG. 2 is a partially sectional perspective view of the detector installed in the glycosylated hemoglobin measuring apparatus shown in FIG. 1. The detector 24 comprises a cell 41, a light-emitting element accommodating part 42 and a light-receiving element accommodating part 43. A disk-form transparent plate 45 and a circular lens 46 are disposed between the cell 41 and the light-emitting element accommodating part 42. Similarly, a disk-form transparent plate 47 and a circular lens 48 are disposed between the cell 41 and the light-receiving element accommodating part 43. An O-ring 51 used as a lens retainer is interposed between the light-emitting element accommodating part 42 and the lens 46, and another O-ring 52 used as a lens retainer is interposed between the light-receiving element accommodating part 43 and the lens 48. The radial cross section of the O-rings 51 and 52 is circular. Furthermore, a halogen lamp for example is disposed as a light-emitting element in the light-emitting element accommodating part 42, and a photodiode or photo-transistor for example is disposed as a light-receiving element in the light-receiving element accommodating part 43, although these parts are omitted from the figures for the sake of simplicity. A packing (not shown) is interposed between the cell 41 and the light-emitting element accommodating part 42, and another packing (not shown) is also interposed between the cell 41 and the light-receiving element accommodating part 43.

The cell 41A is internally provided with a supply flow path 56 for introducing the eluate from the column 23 into the cell 41, a measurement flow path 55 for providing a light path for the measurement of the absorbance of the eluate, an eddy current generating path 58 for generating an eddy current inside the measurement flow path 55, and a discharge flow path 57 for conducting the eluate having passed through the measurement flow path 55 to the outside of the detector 24. Not only the eluate from the column 23, but also light rays of a specified wavelength with which the light-receiving element accommodated in the light-receiving element accommodating part 43 is irradiated by the light-emitting element accommodated in the light-emitting element accommodating part 42, pass through the measurement flow path 55. Accordingly, in order to ensure a light path, the transparent plate 45 and transparent plate 47 that are disposed in contact with the cell 41 may be transparent overall, or only the portions corresponding to the measurement flow path 55 formed inside the cell 41, i.e., the portions near the center of each plate, may be transparent.

Figure 3:
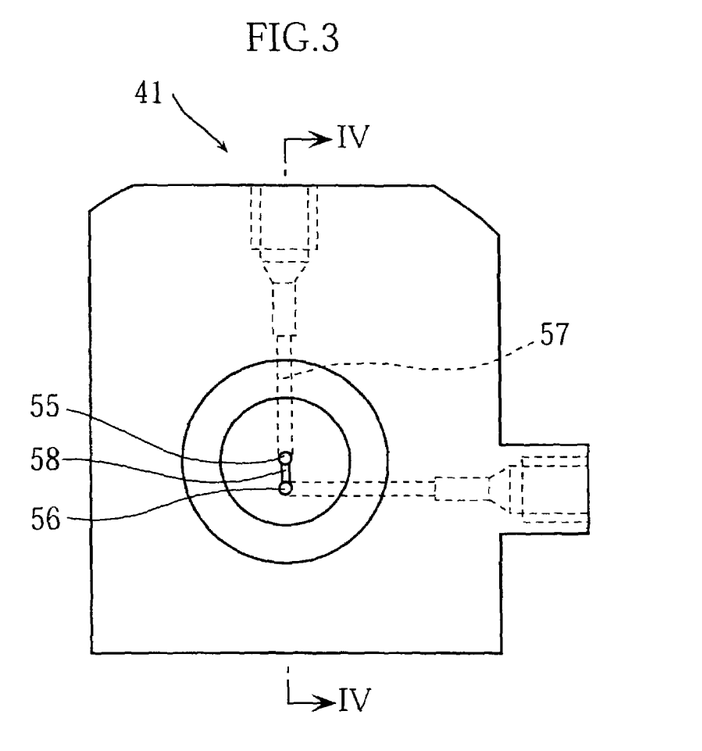
FIG. 3 is a front view of the cell installed in the detector shown in FIG. 2.
Figure 4:
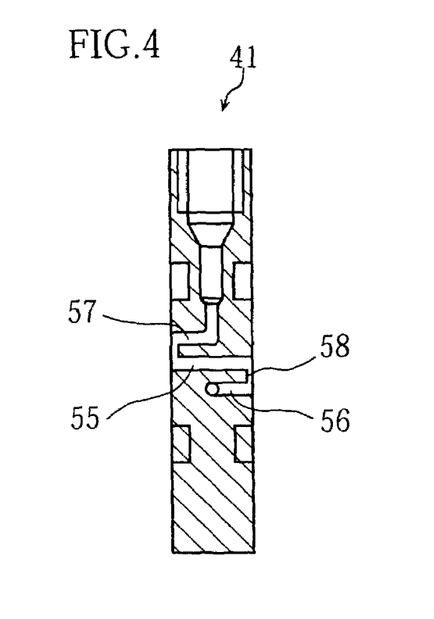
FIG. 4 is a sectional view along lines IV-IV in FIG. 3.

FIG. 3 is a front view of the cell 41 installed in the detector shown in FIG. 2. FIG. 4 is a sectional view along lines IV-IV in FIG. 3. As is shown in FIG. 4, the measurement flow path 55 passes through roughly the central portion of the cell 41 in the direction of thickness, and is formed in a rectilinear configuration. The starting end of the measurement flow path 55 opens on the front surface side of the cell 41, and the terminating end of the measurement flow path 55 opens on the back surface side of the cell 41. As is shown by the broken lines in FIG. 3, the supply flow path 56 extends rectilinearly from the right end surface of the cell 41 to a point beneath the measurement flow path 55, where the supply flow path 56 bends at right angles, and then extends rectilinearly to the front surface side of the cell 41 as shown in FIG. 4. The supply flow path 56 communicates with the starting end of the measurement flow path 55 via the eddy current generating path 58. As is shown in FIG. 4, the discharge flow path 57 extends upward from the terminating end of the measurement flow path 55 along the back surface side of the cell 41. The discharge flow path 57 then bends at right angles and extends toward the front surface side of the cell 41, after which the discharge flow path 57 again bends at right angles and extends rectilinearly to the upper surface of the cell 41.

Figure 5:
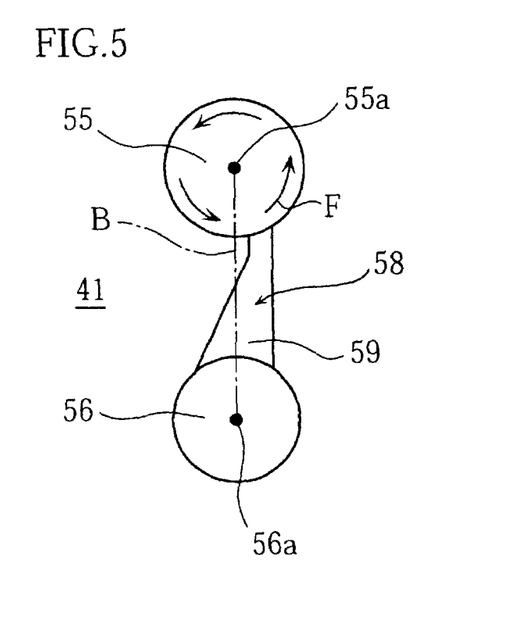
FIG. 5 is an enlarged view of the vicinity of the eddy current generating path of the cell shown in FIG. 3.

FIG. 5 is an enlarged view of the vicinity of the eddy current generating path 58 in the front view of the cell 41 shown in FIG. 3. The front surface of the cell 41A is formed with a groove 59 which extends from the terminating end of the supply flow path 56 to the starting end of the measurement flow path 55, so that a portion of the eddy current flow path 58 is defined by this groove 59. The groove 59 opens on the front surface side of the cell 41. As is shown in FIG. 2, when the transparent plate 47 is placed in contact with the front surface side of the cell 41, a space that is closed off except at both ends is defined by the groove 59 and transparent plate 47. Thus, the transparent plate 47 defines another portion of the eddy current generating path 58. As is shown in FIG. 5, substantially the entire groove 59 is tapered shape and inclined with respect to the line segment B that connects the axis 56a of the supply flow path 56 and the axis 55a of the measurement flow path 55. Accordingly, the end of the eddy current generating path 58 which is open to the measurement flow path 55 is offset from the line segment B toward a peripheral portion of the measurement flow path 55. Furthermore, the end portion of the groove 59 that is open to the measurement flow path 55 is substantially parallel to the line segment B. Consequently, the end portion of the eddy current generating path 58 that is open to the measurement flow path 55 crosses the liquid flow direction inside the measurement flow path 55 roughly at a right angle. The cross-sectional shape of the groove 59 in a sectional plane perpendicular to the liquid flow direction in the eddy current generating path 58 is semicircular both in the tapered portion and in the open portion.

The hemoglobin measuring apparatus incorporating the above-described detector as a liquid homogenizing unit operates as follows. First, sample preparation is performed under the control of the controller 4 which controls the respective parts of the sample preparation section 11. Specifically, a specified amount of blood is drawn in from the analyte accommodating container (not shown) and diluted at a specified dilution rate by a specified diluent before being stored in a dilution tank (not shown) disposed inside the sample preparation section 11. Then, under the control of the controller 4, the injection valve 3 shown in FIG. 1 assumes a state in which the ports 3a and 3b communicate with each other, the ports 3c and 3d communicate with each other, and the ports 3e and 3f communicate with each other. The pump 12 causes the thus prepared blood sample to be introduced into the injection loop 31 from the dilution tank of the sample preparation section 11 via the ports 3e and 3f of the injection valve 3. In cases where the sample exceeds the specified amount and overflows from the injection loop 31, the excess sample returns to the dilution tank of the sample preparation section 11 via the ports 3c and 3d.

Next, the control part 4 causes the injection valve 3 to assume a state in which the ports 3b and 3c communicate with each other, the ports 3d and 3e communicate with each other, and the ports 3f and 3a communicate with each other. Then, the liquid feeding pump 22 feeds an eluant to the port 3b of the injection valve 3 from a selected one of the plural eluant tanks (not shown) of the eluant preparation section 21. The eluant flows into the column 23 via the port 3c, injection loop 31, port 3f and port 3a. The sample which has been temporarily held inside the injection loop 31 is impelled by the eluant into the column 23.

At this time, the liquid feeding pump 12 supplies a cleaning liquid through the port 3e of the injection valve 3 from a cleaning liquid tank (not shown). The cleaning liquid reaches the dilution tank of the sample preparation section 11 through the port 3d as a discharge liquid. As a result, the sample remaining in the sample flow path in the sample pre-treatment section 1 is removed by the cleaning solution. Following such cleaning, the next measurement blood sample is prepared by dilution and the like in the sample pre-treatment section 1 in the same manner as described above.

Furthermore, after the sample temporarily held inside the injection loop 31 is caused to flow into the column 23 by the eluant, the connection state of the injection valve 3 is switched by the controller 4. As a result, the injection valve 3 assumes a state in which the ports 3a and 3b communicate with each other, the ports 3c and 3d communicate with each other, and the ports 3e and 3f communicate with each other. Consequently, the eluant fed out into the port 3b of the injection valve 3 from the eluant preparation section 21 by the pump 22 flows out from the injection valve 3 via the port 3a without passing through the injection loop 31, and is supplied to the column 23.

The sample injected into the column 23 together with the eluant is developed through the column 23 by the eluant which acts as the mobile phase. Due to the differences in adsorption between the respective hemoglobin components contained in the sample and the column 23, the respective hemoglobin components are separated by the column 23. The eluate from the column 23 is supplied to the detector 24 which is installed downstream from the column 23. The absorbance of the eluate passing through the measurement flow path 55 inside the detector 24 is measured by the detector 24. The absorbance measurement utilizes a light wavelength at which the respective hemoglobin components show absorption. Detection signals from the detector 24 are input into the controller 4. On the basis of the absorbance values measured for the respective hemoglobin components such as HbA1ab, HbF, HbA1c, HbA0 and the like contained in the blood, a chromatogram originating from these components is printed on recording paper to indicate the measurement results. The ratios of the respective components that are present are also calculated, and these ratios are displayed as the measurement results.

The eluate that has passed through the detector 24 is discharged into a waste liquid accommodating equipment located outside the apparatus. The waste liquid that is drawn into the waste liquid section 5 is also discharged into the waste liquid accommodating equipment located outside the apparatus.

In the glycosylated hemoglobin measuring apparatus, the eddy current generating path 58 is installed between the measurement flow path 55 in which absorbance measurements are performed in the detector 24 and the supply flow path 56 which is used to introduce the eluate into the detector 24. Accordingly, during the operation of the above-mentioned apparatus, the eluate from the column 23 first flows into the detector 24 from the supply flow path 56, and then reaches the measurement flow path 55 via the eddy current generating path 58. The eddy current generating path 58 shown in FIG. 5 is inclined with respect to the line segment B that connects the axis 56a of the supply flow path 56 and the axis 55a of the measurement flow path 55. Accordingly, the end portion of the eddy current generating path 58 which is open to the measurement flow path 55 is positioned offset from the line segment B toward a peripheral portion of the measurement flow path 55. Consequently, the eluate flowing through the measurement flow path 55 is given a rotating component in the cross section of the flow path. More concretely, at the starting end of the measurement flow path 55, the eluate enters the measurement flow path 55 offset from the axis 55a, so that the eluate flows while instantaneously describing a spiral configuration. Thus, due to the eddy current generating path 58, an eddy current is generated in the eluate flowing through the measurement flow path 55, as indicated by the arrow F in FIG. 5. Furthermore, the eddy current generating path 58 shown in FIG. 5 is tapered toward the measurement flow path 55 substantially over the entire length thereof. Accordingly, the flow velocity of the eluate increases while the eluate flows from the supply flow path 56 to the measurement flow path 55. This increase in speed contributes to the formation of a good eddy current inside the measurement flow path 55. Moreover, since the portion of the eddy current generating path 58 that is located near the terminating end of the eddy current generating path 58 communicates with the measurement flow path 55 roughly at a right angle, the flow component of the eluate flow that is oriented in the path direction of the measurement flow path 55 at the instance of flowing into the measurement flow path 55 from the eddy current generating path 58 is suppressed, so that convecting diffusion in this direction is also suppressed.

When an eddy current is positively generated in the eluate flowing through the measurement flow path 55 as described above, any hemoglobin components contained in the eluate are quickly diffused in the cross section of the flow path of the eluate. If the concentration of the eluate flowing through the measurement flow path 55 is thus equalized in the cross-sectional direction of the flow path so that the problem of a concentration gradient is eliminated or alleviated, the measured value of the absorbance becomes constant. As a result, as long as the sample originates from the same blood analyte, the glycosylated hemoglobin measuring apparatus of the present invention can output a constant measured value with respect to the HbA1c ratio regardless of the concentration of the sample. Furthermore, since diffusion of the components of the eluate in the flow direction inside the measurement flow path 55 is suppressed, re-mixing of the respective hemoglobin components separated by the column 23 can be suppressed. As a result, there is no drop in the resolution of the column 23 appearing in the chromatogram, so that the inherent analytical capacity of the apparatus can be maintained at a high level. Moreover, since this suppression of the diffusion of the components in the flow direction of the eluate suppresses any increase in the half-value width of the respective peaks in the chromatogram, this also contributes to a shortening of the time required for analysis.

Figure 6:
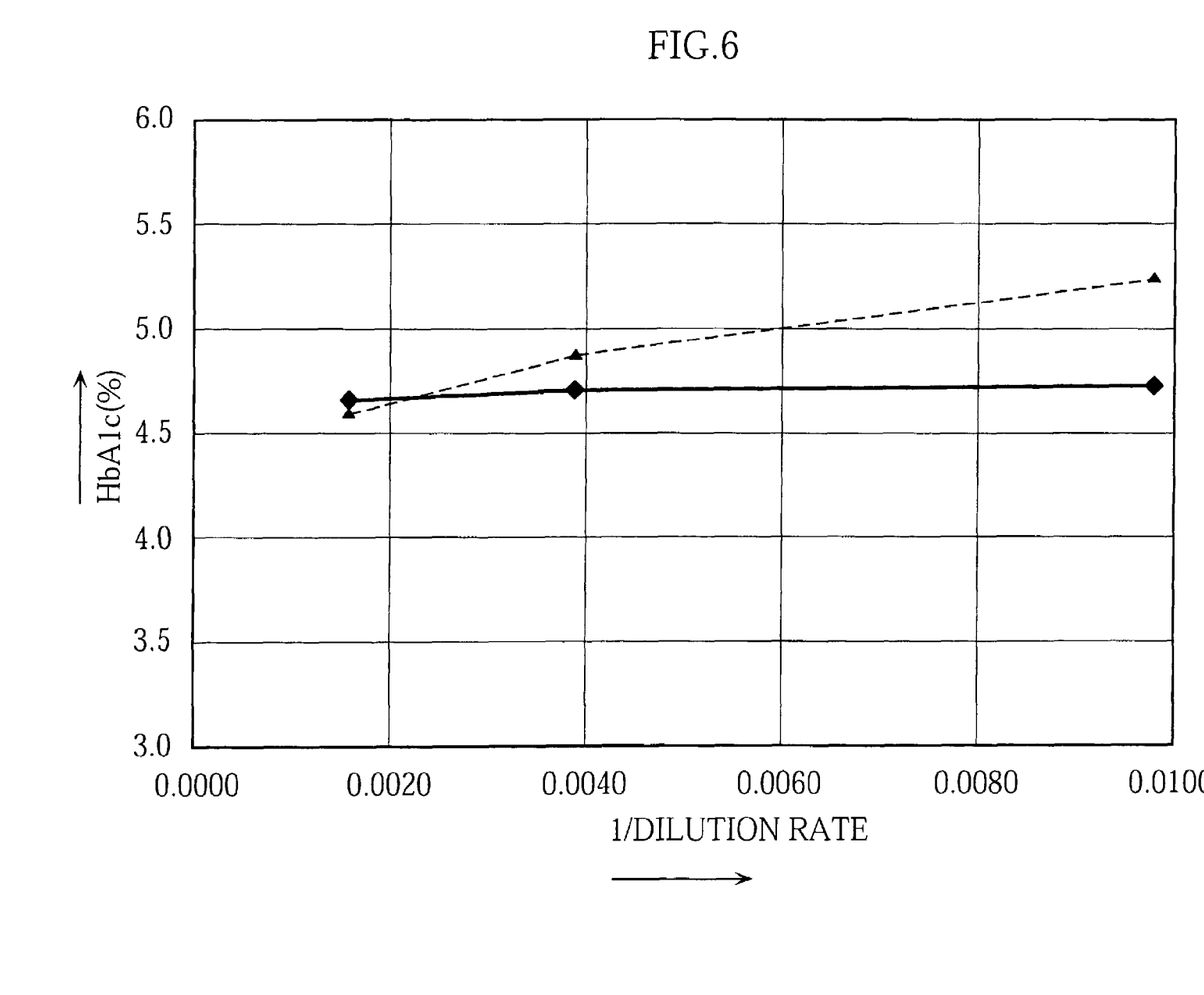
FIG. 6 is a graph which shows the relationship between the dilution rate of the blood as a testing analyte and the measured value of HbA1c.

FIG. 6 is a graph which shows the relationship between the dilution rate of the blood analyte and the measured value of HbA1c. The abscissa shows the reciprocal of the dilution rate of the blood, whereas the ordinate shows the proportion of HbA1c relative to the total amount of hemoglobin contained in the blood. In FIG. 6, the solid line indicates the measurement results obtained by the glycosylated hemoglobin measuring apparatus of the foregoing embodiment, from which it is seen that the measured value of the proportion of HbA1c present is substantially constant. On the other hand, the broken line indicates the measurement results obtained using a conventional glycosylated hemoglobin measuring apparatus not equipped with a diffusion coil, from which it is seen that the measured value of the proportion of HbA1c increases as the dilution rate drops. As is clear from FIG. 6, if the glycosylated hemoglobin measuring apparatus of the present embodiment is used, the variation in the measured value of HbA1c relative to the variation in the dilution rate of the blood is far smaller than that seen in cases where a conventional glycosylated hemoglobin measuring apparatus not equipped with a diffusion coil is used. Furthermore, although the variation in the measured value of HbA1c relative to the variation in the dilution rate of the blood is relatively small in cases where a conventional glycosylated hemoglobin measuring apparatus equipped with a diffusion coil is used, it has been experimentally confirmed that the analytical capacity for HbA1c and other low-concentration components shows a great drop, and that the analysis time required for the eluted components is greatly increased.

Thus, if the present invention is used, the concentration of the eluate can be equalized in the flow path cross section of the measurement flow path 55. Accordingly, variation in the measured value of HbA1c can be greatly reduced by eliminating measurement error for HbA0 caused by variations in the concentration of the sample. Furthermore, since diffusion of the hemoglobin in the flow direction of the eluate can be effectively suppressed, the drop in the analytical capacity for low-concentration components and increase in the analysis time required for the eluted components caused by the diffusion coil in a conventional glycosylated hemoglobin measuring apparatus can be avoided. As a result, the present invention makes it possible to perform quick and accurate measurements.

Figure 7:
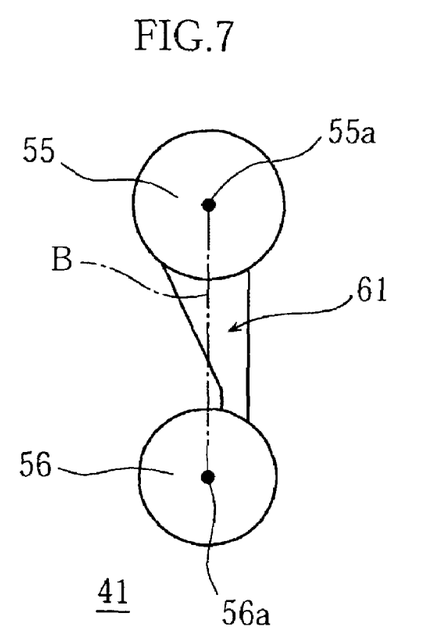
FIG. 7 is an enlarged view of the vicinity of the eddy current generating path in another embodiment of the present invention.
Figure 8:
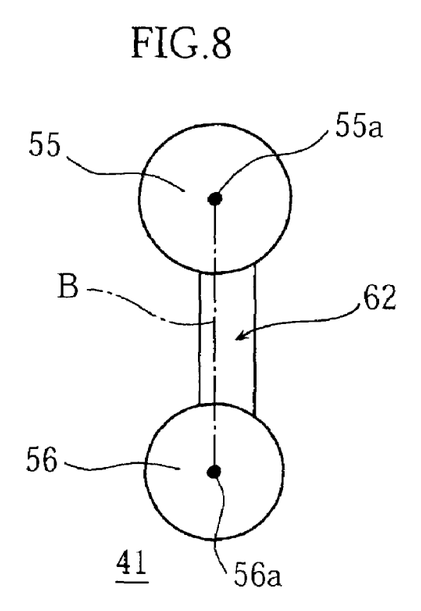
FIG. 8 is an enlarged view of the vicinity of the eddy current generating path in a further embodiment of the present invention.

In the present embodiment shown in FIG. 5, the eddy current generating path 58 gradually tapers from the supply flow path 56 toward the measurement flow path 55. However, in lieu of the eddy current generating path 58, it would also be possible to install an eddy current generating path 61 which flares gradually from the supply flow path 56 toward the measurement flow path 55, as shown in FIG. 7. This eddy current generating path 61 is inclined with respect to the line segment B that connects the axis 56a of the supply flow path 56 and the axis 55a of the measurement flow path 55. Furthermore, as shown in FIG. 8, it would also be possible to install an eddy current generating path 62 which has a uniform flow cross-sectional area from the terminating end of the supply flow path 56 to the starting end of the measurement flow path 55. This eddy current generating path 62 is parallel to and offset from the line segment B that connects the axis 56a of the supply flow path 56 and the axis 55a of the measurement flow path 55. Specifically, the eddy current generating path 62 is formed so that the axis 62a of the eddy current generating path 62 has torsional relationship with respect to the axis 56a of the supply flow path 56 and the axis 55a of the measurement flow path 55. Furthermore, it is desirable that the cross-sectional area of the eddy current generating path 62 be smaller than that of the measurement flow path 55 or of the supply flow path 56.

Figure 9:
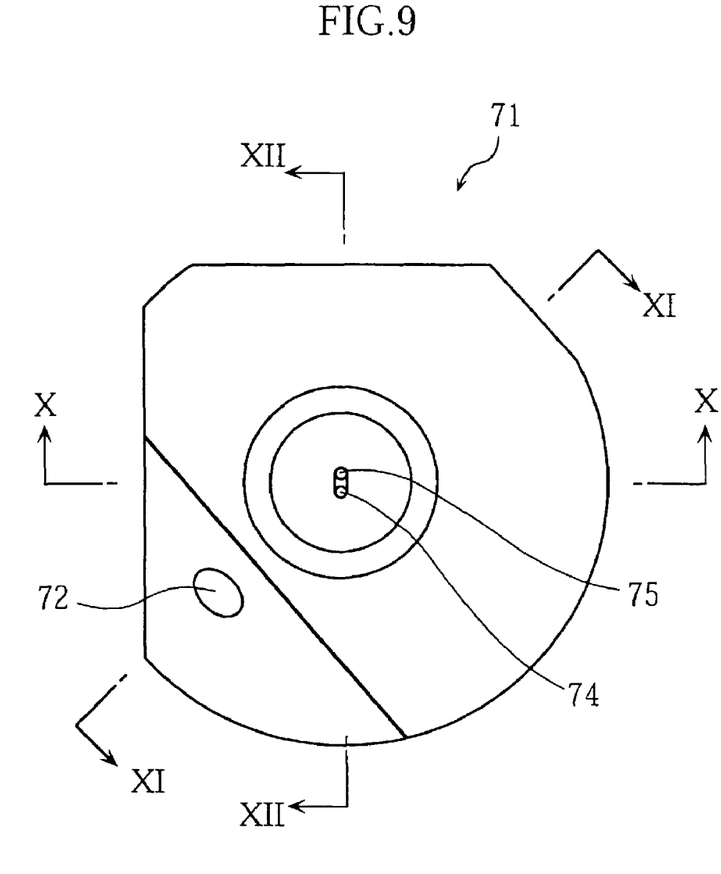
FIG. 9 is a front view of the cell in still another embodiment of the present invention.
Figure 10:
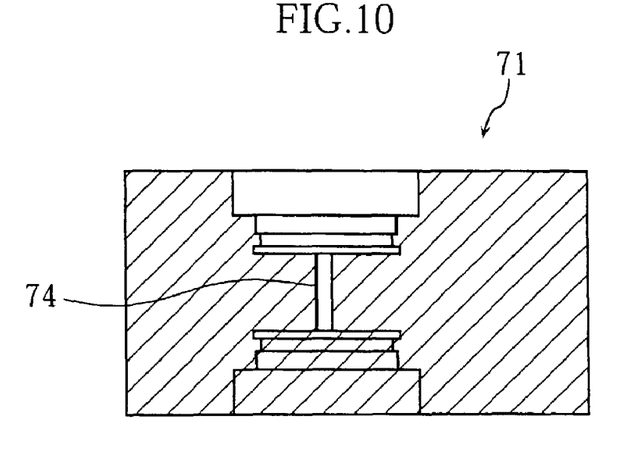
FIG. 10 is a sectional view along lines X-X of the cell shown in FIG. 9.
Figure 11:
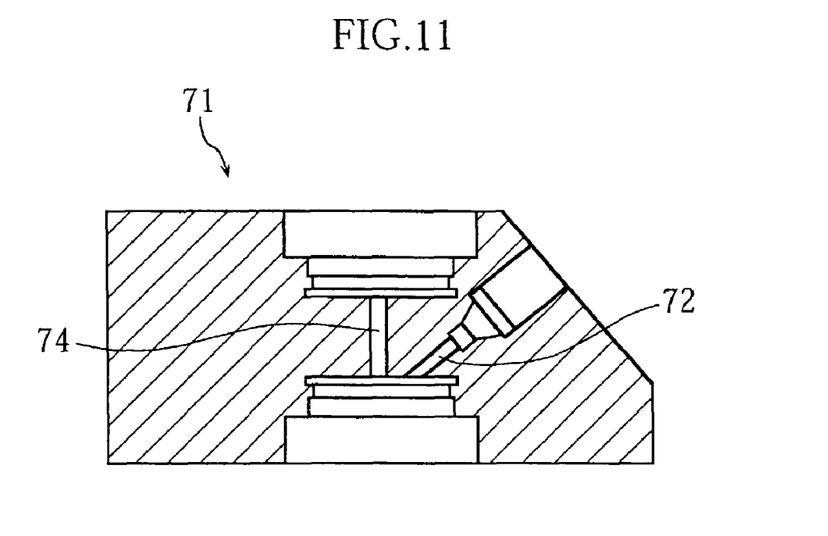
FIG. 11 is a sectional view along lines XI-XI of the cell shown in FIG. 9.
Figure 12:
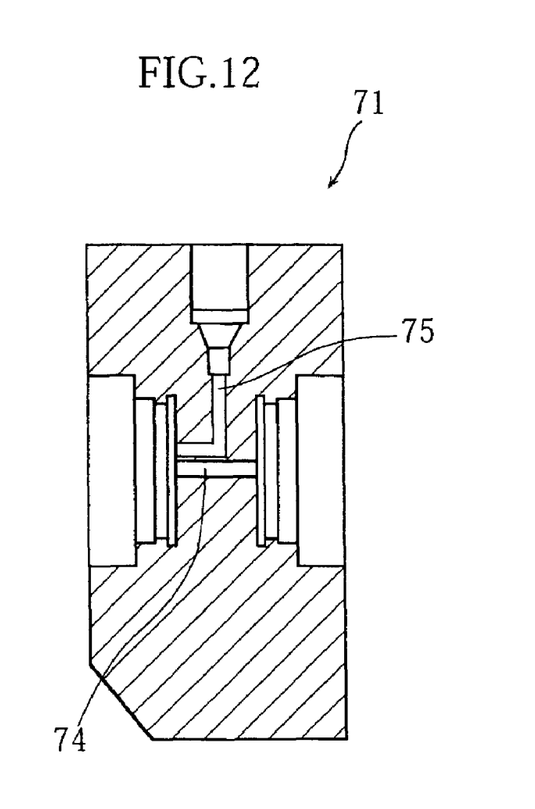
FIG. 12 is a sectional view along lines XII-XII of the cell shown in FIG. 9.
Figure 13:
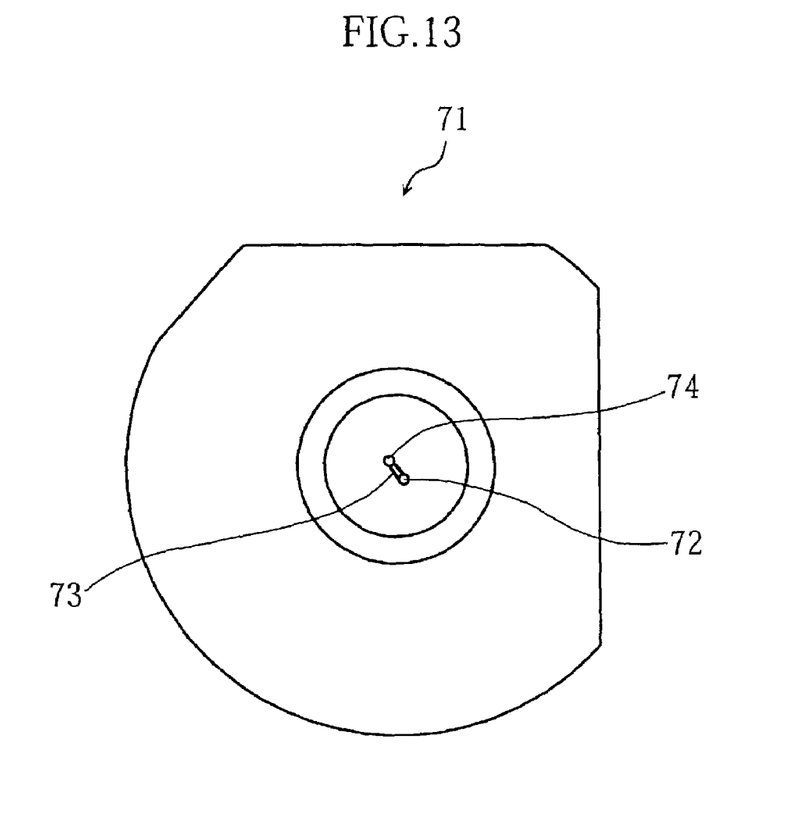
FIG. 13 is a back view of the cell shown in FIG. 9.
Figure 14:
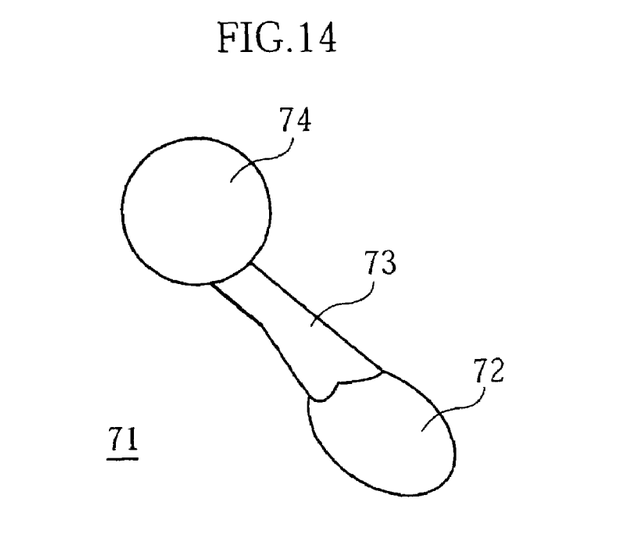
FIG. 14 is an enlarged view of the vicinity of the eddy current generating path in the cell shown in FIG. 9.

FIG. 9 is a front view of the cell 71 of another embodiment. FIG. 10 is a sectional view along lines X-X of the cell 71 shown in FIG. 9. FIG. 11 is a sectional view along lines XI-XI of the cell 71 shown in FIG. 9. FIG. 12 is a sectional view along lines XII-XII of the cell 71 shown in FIG. 9. FIG. 13 is a rear view of the cell 71 shown in FIG. 9. FIG. 14 is an enlarged view of the vicinity of the eddy current generating path in the cell 71 shown in FIG. 9.

The cell 71 comprises a supply flow path 72 for receiving the eluate from the column, a measurement flow path 74 for providing a light path for the measurement of the absorbance of the eluate, an eddy current generating path 73 for conducting the eluate from the supply flow path 72 to the measurement flow path 74 while generating an eddy current inside the measurement flow path 74, and a discharge flow path 75 for discharging the eluate following the measurement of the absorbance. As may be seen from FIGS. 11 and 14, the supply flow path 72 and eddy current generating path 73 are not perpendicular to each other in the cell 71. The supply flow path 72 and eddy current generating path 73 are connected at the point of intersection so that the flow of the eluate forms an angle of approximately 135 degrees. Thus, in the present embodiment, the directional change of flow of the eluate that occurs when the eluate flows into the eddy current generating path 73 from the supply flow path 72 is gradual compared to the variation that occurs in the previously described cell 41. Accordingly, the dynamic pressure of the eluate in the vicinity of the intersection between the supply flow path 72 and eddy current generating path 73 is relaxed, so that the eluate flows smoothly through the overall flow path of the apparatus in which the cell 71 is mounted. Furthermore, the diffusion of the hemoglobin in the flow direction caused by convection of the eluate prior to the flow of the eluate into the measurement flow path 74 is reduced. The remaining construction is substantially similar to that of the cell 41, so that the cell 71 of the present embodiment has merits similar to those obtained in cases where the cell 41 is used.

Thus, in the present embodiment as well, the concentration of the eluate can be equalized in the flow path cross section of the measurement flow path 72. Accordingly, the variation in the measured value of HbA1c can be greatly reduced by eliminating error in the measurement of HbA0 caused by variation in the concentration of the sample. In addition, since the diffusion of the hemoglobin in the flow direction of the eluate can be further suppressed, the drop in the analytical capacity for low-concentration components and the increase in the analysis time required for eluted components that are caused by the diffusion coil in a conventional glycosylated hemoglobin measuring apparatus can be avoided.

The overall construction of the glycosylated hemoglobin measuring apparatus, the concrete constructions of the detector 24 and cells 41 and 71, and the concrete shapes of the eddy current generating paths 58 and 73, are not limited to the foregoing embodiments alone.

In the embodiments, the liquid homogenizing unit comprising a supply flow path, an eddy current generating path, a measurement flow path and a discharge flow path is utilized by its incorporation into a high-performance liquid chromatography apparatus. However, the liquid homogenizing unit of the present invention may also be utilized in other types of apparatus besides a high-performance liquid chromatography apparatus. Furthermore, the high-performance liquid chromatography apparatus in which the liquid homogenizing unit of the present invention is mounted may be constructed as a measuring apparatus other than a glycosylated hemoglobin measuring apparatus.

The invention claimed is:

1. A liquid homogenizing unit comprising:
    a cell including a front surface and a back surface opposite to the front surface;
    a supply flow path and a discharge flow path;
    a first intermediate flow path which communicates with the supply flow path;
    a substantially cylindrical second intermediate flow path which communicates with the first intermediate flow path and the discharge flow path;
    a first cover body disposed on the front surface of the cell; and
    a second cover body disposed on the back surface of the cell;
    wherein the supply flow path, the discharge flow path, the first intermediate flow path and the second intermediate flow path are formed integrally in the cell,
    wherein the first intermediate flow path extends in an intersecting direction relative to the second intermediate flow path,
    wherein the second intermediate flow path extends rectilinearly through the cell from the front surface to the back surface, the supply flow path being open toward the front surface, the first intermediate flow path comprising a single groove formed in the front surface, the groove connecting the supply flow path and the second intermediate flow path at the front surface, the groove being connected to the second intermediate flow path at a position that is unaligned with an axis of the second intermediate flow path, the discharge flow path being open toward the back surface and communicating with the second intermediate flow path, the first cover body being arranged to close off the supply flow path, the first intermediate flow path and the second intermediate flow path, the second cover body being arranged to close off the second intermediate flow path and the discharge flow path, wherein the first intermediate flow path includes a first portion that is connected to the supply flow path and a second portion that is connected to the second intermediate flow path, the first portion tapering from the supply flow path toward the second portion, and wherein the second portion has a uniform cross section and is connected to the second intermediate flow path at a position that is offset from an axis of the second intermediate flow path.

2. The liquid homogenizing unit according to claim 1, wherein the second portion of the first intermediate flow path extends at right angles to the second intermediate flow path.

3. The liquid homogenizing unit according to claim 1, wherein the first intermediate flow path has a smaller cross section than the second intermediate flow path.

4. The liquid homogenizing unit according to claim 1, wherein each of the first and second cover bodies has a transparent part that corresponds to at least the second intermediate flow path, and the second intermediate flow path is a measurement flow path for absorbance measurement.

* * * * *